(12) United States Patent
Pai et al.

(10) Patent No.: US 11,964,931 B2
(45) Date of Patent: Apr. 23, 2024

(54) METHOD OF PREPARING DIISOCYANATE COMPOSITION AND OPTICAL LENS

(71) Applicants: SKC CO., LTD., Gyeonggi-do (KR); WOORI FINE CHEM CO., LTD., Gyeonggi-do (KR)

(72) Inventors: Jaeyoung Pai, Gyeonggi-do (KR); Jeongmoo Kim, Gyeonggi-do (KR); Jung Hwan Myung, Gyeonggi-do (KR); Hyuk Hee Han, Gyeonggi-do (KR)

(73) Assignees: SK PUCORE CO., LTD., Ulsan (KR); WOORI FINE CHEM CO., LTD., Gyeonggi-Do (KR)

( * ) Notice: Subject to any disclaimer, the term of this patent is extended or adjusted under 35 U.S.C. 154(b) by 550 days.

(21) Appl. No.: 17/109,805

(22) Filed: Dec. 2, 2020

(65) Prior Publication Data
US 2021/0171443 A1   Jun. 10, 2021

(30) Foreign Application Priority Data

Dec. 5, 2019   (KR) .................. 10-2019-0161047
Dec. 5, 2019   (KR) .................. 10-2019-0161048
Dec. 6, 2019   (KR) .................. 10-2019-0161470

(51) Int. Cl.
*C07C 263/10*   (2006.01)
*B29D 11/00*    (2006.01)
(Continued)

(52) U.S. Cl.
CPC ...... *C07C 263/10* (2013.01); *B29D 11/00442* (2013.01); *C07C 263/20* (2013.01); *C08G 18/7642* (2013.01); *G02B 1/041* (2013.01)

(58) Field of Classification Search
CPC ..... C07C 263/10; C07C 263/20; G02B 1/041; C08G 18/7642; B29D 11/00442
See application file for complete search history.

(56) References Cited

U.S. PATENT DOCUMENTS

2018/0334531 A1* 11/2018 Shin ................. G02B 1/041
2021/0230352 A1   7/2021 Kim et al.

FOREIGN PATENT DOCUMENTS

CN   1931834 A    3/2007
CN   106674056 A  5/2017
(Continued)

OTHER PUBLICATIONS

Office Action issued by the Korean Patent Office dated May 25, 2021.
(Continued)

*Primary Examiner* — Mathieu D Vargot
(74) *Attorney, Agent, or Firm* — IP & T GROUP LLP

(57) ABSTRACT

In the embodiments, an aqueous hydrochloric acid solution instead of hydrogen chloride gas and solid triphosgene instead of phosgene gas may be used in the process of preparing a diisocyanate from a diamine through a diamine hydrochloride. In addition, the embodiments provide processes for preparing a diisocyanate composition and an optical lens of higher quality, in which the reaction temperature of a diamine hydrochloride composition and triphosgene is controlled to a specific range, or a crude diisocyanate composition obtained from the reaction of a diamine hydrochloride composition and triphosgene is distilled at a specific temperature range, or the molar ratio of a diamine hydrochloride and triphosgene is adjusted to a specific range.

10 Claims, 1 Drawing Sheet

(51) Int. Cl.
    *C07C 263/20*     (2006.01)
    *C08G 18/76*     (2006.01)
    *G02B 1/04*     (2006.01)

(56) References Cited

FOREIGN PATENT DOCUMENTS

| | | |
|---|---|---|
| CN | 106748887 A | 5/2017 |
| CN | 112292413 A | 1/2021 |
| JP | S61-194057 A | 8/1986 |
| JP | 2018-070611 A | 5/2018 |
| KR | 1994-0001948 B1 | 3/1994 |
| KR | 10-1954346 B1 | 3/2019 |

OTHER PUBLICATIONS

Office Action issued by the Korean Intellectual Property Office dated Jan. 26, 2022.
Office Action issued by the China National Intellectual Property Administration for Patent Application No. 202011431043.7 dated Apr. 29, 2022.

\* cited by examiner

[Fig. 1A]
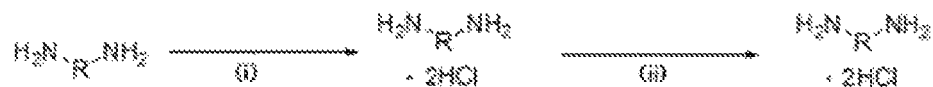
[Fig. 1B]
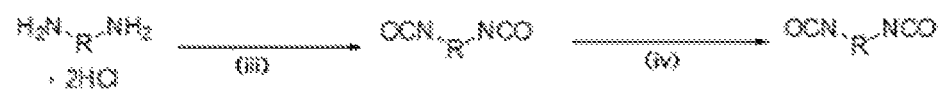
[Fig. 2]
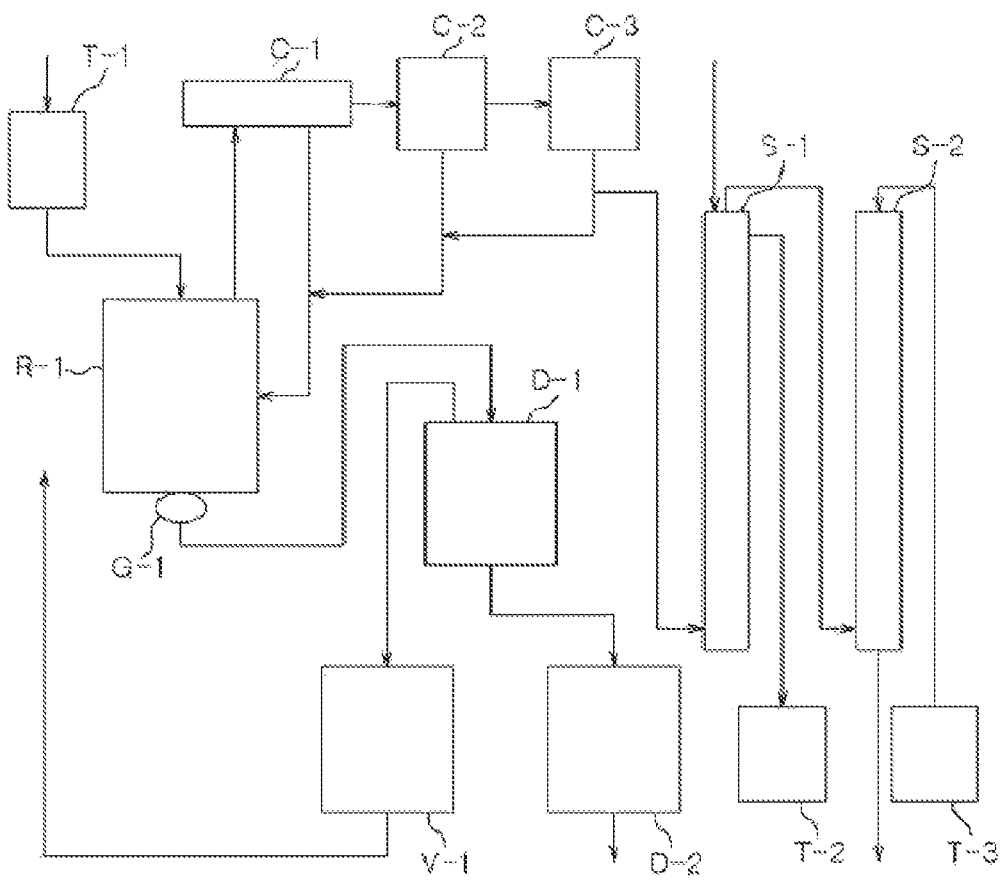

METHOD OF PREPARING DIISOCYANATE COMPOSITION AND OPTICAL LENS

The present application claims priority of Korean patent application numbers 10-2019-0161047 filed on Dec. 5, 2019, 10-2019-0161048 filed on Dec. 5, 2019 and 10-2019-0161470 filed on Dec. 6, 2019, The disclosure of each of the foregoing applications is incorporated herein by reference in its entirety.

TECHNICAL FIELD

Embodiments relate to processes for preparing a diisocyanate composition and an optical lens. More specifically, the embodiments relate to a process for preparing a diisocyanate composition using a diamine hydrochloride composition and a process for preparing an optical lens using the diisocyanate composition.

BACKGROUND ART

Isocyanates used as a raw material for plastic optical lenses are prepared by a phosgene method, a non-phosgene method, a pyrolysis method, or the like.

In the phosgene method, an amine as a raw material is reacted with phosgene ($COCl_2$) gas to synthesize an isocyanate. In addition, in the non-phosgene method, xylylene chloride is reacted with sodium cyanate in the presence of a catalyst to synthesize an isocyanate. In the pyrolysis method, an amine is reacted with an alkyl chloroformate to prepare a carbamate, which is pyrolyzed in the presence of a catalyst at a high temperature to synthesize an isocyanate.

The phosgene method among the above methods for preparing isocyanates is the most widely used. In particular, a direct method in which an amine is directly reacted with phosgene gas has been commonly used. But it has a problem that a plurality of apparatuses for the direct reaction of phosgene gas are required. Meanwhile, in order to supplement the direct method, a hydrochloride method has been developed in which an amine is reacted with hydrogen chloride gas to obtain an amine hydrochloride as an intermediate, which is reacted with phosgene, as disclosed in Korean Patent Publication No. 1994-0001948.

In the method of obtaining hydrochloride as an intermediate by reacting an amine with hydrogen chloride gas among the conventional phosgene methods for synthesizing isocyanates, a hydrochloride is produced as fine particles at atmospheric pressure, so that the agitation inside the reactor is not smoothly carried out. Thus, an additional process of raising the temperature to increase the pressure inside the reactor is required, and there is a problem that the yield of the final product is low as well.

In addition, phosgene gas used in the conventional phosgene method is highly toxic and is a substance subject to environmental regulations. There is a difficulty in storage and management since a separate cooling apparatus is required to store it.

DETAILED DESCRIPTION OF THE INVENTION

Technical Problem

Accordingly, the present inventors have been able to solve the environmental, yield, and quality problems in the conventional process of preparing a diisocyanate, which is mainly used as a raw material for plastic optical lenses, from a diamine through a hydrochloride thereof by way of using an aqueous hydrochloric acid solution instead of hydrogen chloride gas and solid triphosgene instead of phosgene gas while adjusting the reaction conditions.

In addition, the present inventors have focused that the diisocyanate composition obtained through the reaction of a diamine hydrochloride composition and triphosgene contains a hydrolyzable chlorine component, which causes cloudiness and yellowing when a lens is cast. In particular, the present inventors have discovered that since a hydrolyzable chlorine compound such as chloromethylbenzyl isocyanate (CBI) or 1,3-bis(chloromethyl)benzene is produced at high temperatures, it is difficult to remove it unless the temperature of the reaction of a diamine hydrochloride composition and triphosgene is controlled.

Accordingly, an object of the embodiment is to provide processes for preparing a diisocyanate composition and an optical lens of higher quality by controlling the reaction temperature of a diamine hydrochloride composition and triphosgene to a specific range or distilling a crude diisocyanate composition obtained from the reaction of a diamine hydrochloride composition and triphosgene at a specific temperature range.

In addition, the present inventors have focused that the yield and purity of the diisocyanate to be prepared can be enhanced by controlling the amounts of a diamine hydrochloride composition, triphosgene, and an organic solvent employed in the process for preparing a diisocyanate composition. In particular, the present inventors have discovered that if the molar ratio of a diamine hydrochloride composition and triphosgene falls outside a certain range, urea is formed or hydrolyzable chlorine is increased, which may lower the yield and purity of the diisocyanate to be prepared.

Accordingly, an object of the embodiment is to provide processes for preparing a diisocyanate composition and an optical lens capable of enhancing the optical characteristics by controlling the molar ratio of a diamine hydrochloride composition and triphosgene.

Solution to the Problem

According to an embodiment, there is provided a process for preparing a diisocyanate composition, which comprises (1) reacting a diamine with an aqueous hydrochloric acid solution to obtain a diamine hydrochloride composition; and (2) reacting the diamine hydrochloride composition with triphosgene to obtain a diisocyanate composition, wherein the reaction of step (2) is carried out at a temperature of 115° C. to 160° C., or the molar ratio of the diamine hydrochloride composition and triphosgene introduced to the reaction of step (2) is greater than 1:0.70 to less than 0.95.

According to another embodiment, there is provided a process for preparing a diisocyanate composition, which comprises (1) reacting a diamine with an aqueous hydrochloric acid solution to obtain a diamine hydrochloride composition; (2-1) reacting the diamine hydrochloride composition with triphosgene to obtain a crude diisocyanate composition; and (2-2) distilling the crude diisocyanate composition at a temperature of 100° C. to 130° C. or 100° C. to 150° C. to obtain a diisocyanate composition.

According to still another embodiment, there is provided a process for preparing an optical lens, which comprises obtaining a diisocyanate composition from the above preparation process; and mixing the diisocyanate composition with a thiol or an episulfide and polymerizing and curing the resultant in a mold.

Advantageous Effects of the Invention

In the process for preparing a diisocyanate according to the above embodiment, phosgene gas, which is highly toxic and has difficulties in storage and management, is not used. Instead, triphosgene, which is less toxic and does not require a separate cooling storage apparatus since it is solid at room temperature, is used; thus, it is excellent in the handling convenience and processability. In addition, in the process for preparing a diisocyanate according to the above embodiment, an aqueous hydrochloric acid solution, without the use of hydrogen chloride gas, is used to prepare a diamine hydrochloride as an intermediate. Since the reaction can be carried out even at atmospheric pressure, an additional apparatus for high-temperature heating and cooling is not required, and the yield can be enhanced.

In addition, in the process for preparing a diisocyanate composition according to the above embodiment, an aqueous hydrochloric acid solution is used to prepare a diamine hydrochloride composition, so that the final yield can be further enhanced. The selection of raw materials can be broadened since the content of water and impurities in the diamine as a raw material has little impact.

In particular, according to the above embodiment, the reaction temperature of a diamine hydrochloride composition and triphosgene is controlled to a specific range, or a crude diisocyanate composition obtained from the reaction of a diamine hydrochloride composition and triphosgene is distilled at a specific temperature range, which reduces the hydrolyzable chlorine compound such as chloromethylbenzyl isocyanate (CBI) or 1,3-bis(chloromethyl)benzene, thereby preventing a deterioration in the physical properties such as stria, cloudiness, and yellowing of the final optical lens.

In addition, in the process for preparing a diisocyanate composition according to the above embodiment, an aqueous hydrochloric acid solution and an organic solvent are used, while the reaction conditions are adjusted, to prepare a diamine hydrochloride composition, so that the final yield can be further enhanced by preventing the hydrochloride from being dissolved in the aqueous hydrochloric acid solution. The selection of raw materials can be broadened since the content of water and impurities in the diamine as a raw material has little impact.

In particular, according to the above embodiment, the molar ratio of a diamine hydrochloride composition and triphosgene is controlled within a specific range, whereby the yield and purity of the diisocyanate to be prepared can be enhanced. Thus, it is possible to prevent a deterioration in the physical properties such as cloudiness and yellowing of the final optical lens.

Accordingly, the process for preparing a diisocyanate composition according to the embodiment can be applied to the preparation of a plastic optical lens of high quality.

BRIEF DESCRIPTION OF THE DRAWINGS

FIG. 1A and FIG. 1B schematically show the process for preparing a diisocyanate composition according to an embodiment.

FIG. 2 shows an example of the process equipment for the reaction of a diamine hydrochloride and triphosgene.

REFERENCE NUMERALS OF THE DRAWINGS

T-1: first tank, T-2: second tank, T-3: third tank
R-1: reactor, D-1: first distiller, D-2: second distiller
C-1: first condenser, C-2: second condenser, C-3: third condenser
S-1: first scrubber, S-2: second scrubber
G-1: viewing window, V-1: solvent recovery apparatus.

BEST MODE FOR CARRYING OUT THE INVENTION

Throughout the present specification, when a part is referred to as "comprising" an element, it is understood that other elements may be comprised, rather than other elements are excluded, unless specifically stated otherwise.

In addition, all numbers and expression related to the physical properties, contents, dimensions, and the like used herein are to be understood as being modified by the term "about," unless otherwise indicated.

In the present specification, an "amine" refers to a compound having one or more amine groups at the terminal, and a "diamine" refers to a compound having two amine groups at the terminal. They may have a wide variety of structures depending on the skeleton of an aliphatic chain, an aliphatic ring, and an aromatic ring. Specific examples of the diamine include xylylenediamine (XDA), hexamethylenediamine (HDA), 2,2-dimethylpentanediamine, 2,2,4-trimethylhexanediamine, butenediamine, 1,3-butadiene-1,4-diamine, 2,4,4-trimethylhexamethylenediamine, bis(aminoethyl)carbonate, 4,4'-methylenediamine (MDA), bis(aminoethyl) ether, bis(aminoethyl)benzene, bis(aminopropyl)benzene, α,α,α',α'-tetramethylxylylenediamine, bis(aminobutyl)benzene, bis(aminomethyl)naphthalene, bis(aminomethyl)diphenyl ether, bis(aminoethyl)phthalate, 2,6-di(aminomethyl)furan, hydrogenated xylylenediamine (H6XDA), dicyclohexylmethanediamine, cyclohexanediamine, methylcyclohexanediamine, isophoronediamine (IPDA), dicyclohexyldimethylmethanediamine, 2,2-dimethyldicyclohexylmethanediamine, 2,5-bis(aminomethyl)bicyclo-[2,2,1]-heptane, 2,6-bis(aminomethyl)bicyclo-[2,2,1]-heptane, 3,8-bis(aminomethyl)tricyclodecane, 3,9-bis(aminomethyl)tricyclodecane, 4,8-bis(aminomethyl)tricyclodecane, 4,9-bis(aminomethyl)tricyclodecane, norbornenediamine (NBDA), bis(aminomethyl) sulfide, bis(aminoethyl) sulfide, bis(aminopropyl) sulfide, bis(aminohexyl) sulfide, bis(aminoethyl) sulfone, bis(aminomethyl) disulfide, bis(aminoethyl) disulfide, bis(aminopropyl) disulfide, bis(aminomethylthio) methane, bis(aminoethylthio)methane, bis(aminoethylthio) ethane, and bis(aminomethylthio)ethane. More specifically, the diamine may be at least one selected from the group consisting of xylylenediamine (XDA), norbornenediamine (NBDA), hydrogenated xylylenediamine (H6XDA), isophoronediamine (IPDA), and hexamethylenediamine (HDA). The xylylenediamine (XDA) includes orthoxylylenediamine (o-XDA), metaxylylenediamine (m-XDA), and paraxylylenediamine (p-XDA).

In the present specification, an "isocyanate" refers to a compound having an NCO group, a "diisocyanate" refers to a compound having two NCO groups at the terminal. They may have a wide variety of structures depending on the skeleton of an aliphatic chain, an aliphatic ring, and an aromatic ring. Specific examples of the diamine include xylylene diisocyanate (XDI), hexamethylene diisocyanate (HDI), 2,5-bis(isocyanatomethyl)-bicyclo[2.2.1]heptane, 2,6-bis(isocyanatomethyl)-bicyclo[2.2.1]heptane, hydrogenated xylylene diisocyanate (H6XDI), dicyclohexylmethane diisocyanate, isophorone diisocyanate (IPDI), 1,2-diisocyanatobenzene, 1,3-diisocyanatobenzene, 1,4-diisocyanatobenzene, 2,4-diisocyanatotoluene, ethylphenylene diisocyanate, dimethylphenylene diisocyanate, biphenyl diisocyanate, toluidine diisocyanate, 4,4'-methylenebis(phenylisocyanate) (MDI), 1,2-bis(isocyanatomethyl)benzene, 1,3-bis(isocyanatomethyl)benzene, 1,4-bis(isocyanatomethyl)benzene, 1,2-bis(isocyanatoethyl)benzene, 1,3-bis (isocyanatoethyl)benzene, 1,4-bis(isocyanatoethyl)benzene, α,α,α',α'-tetramethylxylylene diisocyanate, bis(isocyanatomethyl)naphthalene, bis(isocyanatomethylphenyl) ether, norbornene diisocyanate (NBDI), bis(isocyanatomethyl) sulfide, bis(isocyanatoethyl) sulfide, bis(isocyanatopropyl) sulfide, 2,5-diisocyanatotetrahydrothiophene, 2,5-diisocyanatomethyltetrahydrothiophene, 3,4-diisocyanatomethyltetrahydrothiophene, 2,5-diisocyanato-1,4-dithiane, and 2,5-diisocyanatomethyl-1,4-dithiane. More specifically, the diisocyanate may be at least one selected from the group consisting of xylylene diisocyanate (XDI), norbornene diisocyanate (NBDI), hydrogenated xylylene diisocyanate (H6XDI), isophorone diisocyanate (IPDI), and hexamethylene diisocyanate (HDI). The xylylene diisocyanate (XDI) includes orthoxylylene diisocyanate (o-XDI), metaxylylene diisocyanate (m-XDI), and paraxylylene diisocyanate (p-XDIA).

In the present specification, as is well known, a "composition" may refer to a form in which two or more chemical components are mixed or combined in a solid, liquid, and/or gas phase while generally maintaining their respective unique properties.

The compounds used in each reaction step according to the above embodiment (e.g. triphosgene) or the compounds obtained as a result of the reaction (e.g., diamine hydrochloride, diisocyanate) are generally present in a mixed or combined state with heterogeneous components produced as unreacted raw materials in each reaction step, as side reactions or reaction with water, or as natural decomposition of the compounds. A trace amount of these components may remain to exist with the main components.

According to the embodiment, since attention is paid to these heterogeneous components mixed or combined with the main compounds, even a trace amount of the heterogeneous components is treated as a composition mixed or combined with the main compounds to specifically illustrate the components and contents thereof.

In addition, in the present specification, for clear and easy distinction between various compositions, terms are also described in combination with the names of the main components in the composition. For example, a "diamine hydrochloride composition" refers to a composition comprising a diamine hydrochloride as a main component, and a "diisocyanate composition" refers to a composition comprising a diisocyanate as a main component. In such event, the content of the main component in the composition may be 50% by weight or more, 80% by weight or more, or 90% by weight or more, for example, 90% by weight to 99.9% by weight.

[Process for Preparing a Diisocyanate Composition]

According to an embodiment, there is provided a process for preparing a diisocyanate composition, which comprises (1) reacting a diamine with an aqueous hydrochloric acid solution to obtain a diamine hydrochloride composition; and (2) reacting the diamine hydrochloride composition with triphosgene to obtain a diisocyanate composition, wherein the reaction of step (2) is carried out at a temperature of 115° C. to 160° C., or the molar ratio of the diamine hydrochloride composition and triphosgene introduced to the reaction of step (2) is greater than 1:0.70 to less than 0.95.

The process for preparing a diisocyanate composition according to an embodiment comprises (1) reacting a diamine with an aqueous hydrochloric acid solution to obtain a diamine hydrochloride composition; and (2) reacting the diamine hydrochloride composition with triphosgene at a temperature of 115° C. to 160° C. to obtain a diisocyanate composition.

The process for preparing a diisocyanate composition according to another embodiment comprises (1) reacting a diamine with an aqueous hydrochloric acid solution to obtain a diamine hydrochloride composition; and (2) reacting the diamine hydrochloride composition with triphosgene to obtain a diisocyanate composition, wherein the molar ratio of the diamine hydrochloride composition and triphosgene introduced to the reaction of step (2) is greater than 1:0.70 to less than 0.95.

The process for preparing a diisocyanate composition according to still another embodiment comprises (1) reacting a diamine with an aqueous hydrochloric acid solution to obtain a diamine hydrochloride composition; (2-1) reacting the diamine hydrochloride composition with triphosgene to obtain a crude diisocyanate composition; and (2-2) distilling the crude diisocyanate composition at a temperature of 100° C. to 130° C. to obtain a diisocyanate composition.

FIG. 1A and FIG. 1B schematically show the process for preparing a diisocyanate composition according to an embodiment. In FIG. 1A and FIG. 1B, R comprises an aromatic ring, an aliphatic ring, an aliphatic chain, and the like. As a specific example, R may be xylylene, norbornene, hydrogenated xylylene, isophorone, or hexamethylene, but it is not limited thereto.

In FIG. 1A, (i) may comprise a step of adding an aqueous hydrochloric acid solution to react a diamine with the aqueous hydrochloric acid solution. In FIG. 1A, (ii) may comprise at least one step selected from a precipitation step, a filtration step, a drying step, and a washing step. In FIG. 1B, (iii) may comprise a step of adding triphosgene to react a diamine hydrochloride composition with triphosgene. In FIG. 1B, (iv) may comprise at least one step selected from a degassing step, a filtration step, and a distillation step.

Hereinafter, each step will be described in detail.

Preparation of a Diamine Hydrochloride Composition

First, a diamine is reacted with an aqueous hydrochloric acid solution to obtain a diamine hydrochloride composition.

In addition, after the reaction of the diamine and the aqueous hydrochloric acid solution, a first organic solvent may be further added to obtain the diamine hydrochloride composition in a solid phase.

The following Reaction Scheme 1 shows an example of the reaction in this step.

[Reaction Scheme 1]

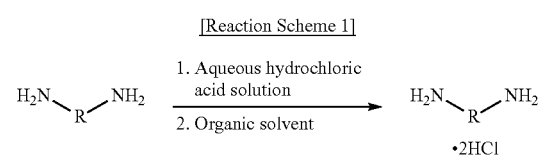

In the above scheme, R comprises an aromatic ring, an aliphatic ring, an aliphatic chain, and the like. As a specific example, R may be xylylene, norbornene, hydrogenated xylylene, isophorone, or hexamethylene, but it is not limited thereto.

In the conventional method in which hydrogen chloride gas is used, a hydrochloride is produced as fine particles upon reaction at atmospheric pressure, so that the agitation inside the reactor is not smoothly carried out. Thus, an additional process of raising the pressure to increase the internal temperature of the reactor is required, and there is a problem that the yield of the final product is low as well.

According to the above embodiment, however, since an aqueous hydrochloric acid solution is used, it is possible to solve the problem involved in the prior art in which hydrogen chloride gas is used. Specifically, when an aqueous hydrochloric acid solution is used, the product obtained through the reaction is in a solid form rather than a slurry form, so that the yield is high. The reaction can be carried out even at atmospheric pressure, so that a separate apparatus or process for rapid cooling is not required.

The concentration of the aqueous hydrochloric acid solution may be 5% by weight to 50% by weight. Within the above concentration range, it is possible to minimize the dissolution of the hydrochloride in the aqueous hydrochloric acid solution, thereby enhancing the final yield, and to improve the handling convenience.

Specifically, the concentration of the aqueous hydrochloric acid solution may be 10% by weight to 45% by weight, 20% by weight to 45% by weight, or 30% by weight to 40% by weight. More specifically, the aqueous hydrochloric acid solution may have a concentration of 20% by weight to 45% by weight.

The diamine and the aqueous hydrochloric acid solution may be introduced to the reaction at an equivalent ratio of 1:2 to 5. If the equivalent ratio is within the above range, it is possible to reduce the unreacted materials and to prevent a reduction in the yield caused by dissolution as water is generated. Specifically, the diamine and the aqueous hydrochloric acid solution may be introduced to the reaction at an equivalent ratio of 1:2 to 2.5.

The introduction of the diamine and the aqueous hydrochloric acid solution may be carried out while the internal temperature of the reactor is maintained to be constant. When the diamine and the aqueous hydrochloric acid solution are introduced, the internal temperature of the reactor may be in the range of 20° C. to 100° C. Within the above temperature range, it is possible to prevent the temperature from being raised above the boiling point, which is not suitable for the reaction, or the temperature from being lowered too much, whereby the reaction efficiency is reduced. Specifically, when the diamine and the aqueous hydrochloric acid solution are introduced, the internal temperature of the reactor may be 20° C. to 60° C., more specifically 20° C. to 40° C. or 40° C. 20 to 60° C.

In the conventional hydrochloride method, a large amount of heat is generated in the reaction, which requires rapid cooling through a separate cooler, whereas the reaction materials are introduced while a low temperature is maintained according to the embodiment, which does not require a separate cooler.

The introduction of the diamine and the aqueous hydrochloric acid solution may be carried out, for example, in a sequence in which the aqueous hydrochloric acid solution may be first introduced to the reactor and the diamine may then be slowly introduced to the reactor. The introduction of the diamine and/or the aqueous hydrochloric acid solution may be carried out for 30 minutes to 3 hours.

When the introduction of the diamine and the aqueous hydrochloric acid solution is completed, the internal temperature of the reactor may be lowered to 0° C. to 20° C., 0° C. to 10° C., or 10° C. to 20° C.

The reaction between the diamine and the aqueous hydrochloric acid solution may be carried out at atmospheric pressure for, for example, 30 minutes to 2 hours with stirring.

As a result of the reaction between the diamine and the aqueous hydrochloric acid solution, a diamine hydrochloride composition in an aqueous solution form may be obtained as the reaction resultant.

Thereafter, a step of treating the diamine hydrochloride composition may be further carried out. For example, the step of treating the diamine hydrochloride composition may comprise at least one of precipitating the diamine hydrochloride composition, filtering the diamine hydrochloride composition, drying the diamine hydrochloride composition, and washing the diamine hydrochloride composition.

Specifically, a first organic solvent may be introduced to the reaction resultant to precipitate a solid diamine hydrochloride composition. That is, the first organic solvent may induce the precipitation of a solid diamine hydrochloride composition through crystallization. More specifically, the first organic solvent may be introduced to the reaction resultant, which is cooled and further stirred to carry out the reaction.

Specifically, the first organic solvent may be at least one selected from the group consisting of diethyl ether, diisopropyl ether, dioxane, tetrahydrofuran, methanol, ethanol, dimethyl sulfoxide, dimethylformamide, acetonitrile, acetone, trichloroethylene, tetrachloroethane, trichloroethanol, n-butanol, isobutanol, methyl ethyl ketone, methyl butyl ketone, isopropanol, hexane, chloroform, and methyl acetate.

The amount (weight) of the first organic solvent introduced may be 1 to 5 times the weight of the diamine. If the introduced amount is within the above range, it is possible to prevent the use of excessive organic solvents while the yield of the final hydrochloride is high. Specifically, the first organic solvent may be introduced to the reaction in an amount of 1 to 2 times, or 1 to 1.5 times, the weight of the diamine.

After the first organic solvent is introduced, the cooling temperature may be −10° C. to 10° C. or −5° C. to 5° C. In addition, the additional reaction time after cooling may be 30 minutes to 2 hours or 30 minutes to 1 hour.

According to a specific example, the steps of (1a) introducing the aqueous hydrochloric acid solution to a first reactor; (1b) introducing the diamine to the first reactor and stirring them; and (1c) introducing the first organic solvent to the first reactor and stirring them may be sequentially carried out.

More specifically, the process may further comprise cooling the inside of the reactor to a temperature of 0° C. to 10° C. after the introduction of the diamine and before stirring in step (1 b); and cooling the inside of the reactor to a temperature of −5° C. to 5° C. after the introduction of the first organic solvent and before stirring in step (1c).

After the first organic solvent is introduced, separation, filtration, washing, and drying may be further carried out. For example, after the first organic solvent is introduced, the aqueous layer may be separated, filtered, washed, and dried to obtain a solid diamine hydrochloride composition. The washing may be carried out one or more times using, for example, a solvent having a polarity index of 5.7 or less. In addition, the drying may be carried out using vacuum drying. For example, it may be carried out at a temperature of 40° C. to 90° C. and a pressure of 2.0 torr or less.

As a result, the impurities generated in the step of obtaining the diamine hydrochloride composition may be removed together with the first organic solvent. Thus, the process may further comprise removing the impurities generated in the step of obtaining the diamine hydrochloride composition together with the first organic solvent. Impurities are generated in the reaction for preparing the diamine hydrochloride composition and are contained in the first organic solvent. Such impurities may be removed by the step of removing the first organic solvent, whereby the purity of the product may be increased.

According to the above process, a diamine is reacted with an aqueous hydrochloric acid solution, which is then subjected to additional treatment such as precipitation, filtration, drying, and washing, whereby a solid diamine hydrochloride composition can be obtained with high purity. In contrast, in the conventional process in which a diamine is reacted with hydrogen chloride gas in an organic solvent, a slurry of a diamine hydrochloride is obtained, which is not readily purified.

The yield of the diamine hydrochloride composition thus obtained may be 50% or more, 65% or more, 80% or more, 85% or more, or 90% or more, specifically 85% to 95% or 88% to 92%.

Meanwhile, the organic layer can be separated from the reactant and recycled as an organic solvent. Thus, the recovery rate of the first organic solvent may be 80% or more, 85% or more, or 90% or more, specifically 80% to 95% or 80% to 82%.

Diamine Hydrochloride Composition

In the process for preparing a diamine hydrochloride as described above, the diamine is easily degraded by temperature and humidity due to its high reactivity and pH, so that the b* value according to the CIE color coordinate of the diamine hydrochloride composition may be increased. In particular, if a diamine hydrochloride composition having a b* value of a certain level or more is used to prepare a diisocyanate composition, the color and haze may be deteriorated, and it may have an impact on the stria, transmittance, yellow index, and refractive index of the final optical lens. In addition, if distillation is carried out several times in order to make a discolored diisocyanate composition colorless and transparent, it may cause a loss in yield, thereby reducing the economic efficiency.

According to the above embodiment, however, the b* value according to the CIE color coordinate of the diamine hydrochloride composition in water may be adjusted, so that it is possible to enhance the optical characteristics of a diisocyanate composition and an optical lens.

The diamine hydrochloride composition prepared by the process according to the above embodiment has a b* value according to the CIE color coordinate of 1.2 or less when dissolved in water at a concentration of 8% by weight. For example, the b* value according to the CIE color coordinate may be 1.0 or less or 0.8 or less. Specifically, the b* value according to the CIE color coordinate may be 0.1 to 1.2, 0.1 to 1.0, 0.1 to 0.8, or 0.2 to 1.0.

In order to adjust the b* value of the diamine hydrochloride composition, an aqueous hydrochloric acid solution having a content of Fe ions at a certain level or less may be used as a raw material. For example, the content of Fe ions in the aqueous hydrochloric acid solution used for preparing the diamine hydrochloride composition may be 0.5 ppm or less. Specifically, the content of Fe ions in the aqueous hydrochloric acid solution may be 0.3 ppm or less or 0.2 ppm or less. More specifically, the content of Fe ions in the aqueous hydrochloric acid solution may be 0.001 ppm to 0.5 ppm or 0.1 ppm to 0.3 ppm.

Alternatively, the b* value according to the CIE color coordinate of the diamine hydrochloride composition may be adjusted by washing it with a solvent having a polarity index of 5.7 or less. That is, the process for preparing a diamine hydrochloride composition adopted in the above embodiment comprises washing the composition comprising a diamine hydrochloride with a solvent having a polarity index of 5.7 or less to adjust the b* value according to the CIE color coordinate to 1.2 or less when dissolved in water at a concentration of 8% by weight.

In such event, the solvent having a polarity index of 5.7 or less may comprise dichloromethane, and other solvents may be used. In addition, the temperature of the solvent having a polarity index of 5.7 or less may be 0° C. to 5° C.

The diamine hydrochloride composition obtained by the above process mainly comprises a diamine hydrochloride, and the content of the diamine hydrochloride may be 50% by weight to 99.9% by weight, 65% by weight to 99.9% by weight, 80% by weight to 99.9% by weight, or 90% by weight to 99.9% by weight, based on the total weight of the composition. In such event, the diamine hydrochloride may contain two of HCl bonded to the two terminal amine groups of the diamine.

In addition, the content of water in the diamine hydrochloride composition thus obtained may be 5% or less.

Preparation of a Diisocyanate Composition

Next, the diamine hydrochloride composition is reacted with triphosgene to obtain a diisocyanate composition.

Specifically, the diamine hydrochloride composition is reacted with triphosgene to obtain a crude diisocyanate composition, and the crude diisocyanate composition is distilled at a temperature of 100° C. to 130° C. to obtain a diisocyanate composition.

In such event, the reaction of the diamine hydrochloride composition with triphosgene may be carried out in a second organic solvent.

The following Reaction Scheme 2 shows an example of the reaction in this step.

[Reaction Scheme 2]

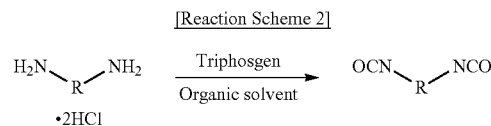

In the above scheme, R comprises an aromatic ring, an aliphatic ring, an aliphatic chain, and the like. As a specific example, R may be xylylene, norbornene, hydrogenated xylylene, isophorone, or hexamethylene, but it is not limited thereto.

Specifically, the diamine hydrochloride composition prepared above is introduced to a second organic solvent, reacted with triphosgene (BTMC, bis(trichloromethyl)carbonate), and then purified to obtain a diisocyanate composition.

Specifically, the second organic solvent may be at least one selected from the group consisting of benzene, toluene, ethylbenzene, chlorobenzene, monochlorobenzene, 1,2-dichlorobenzene (ODCB), dichloromethane, 1-chloro-n-butane, 1-chloro-n-pentane, l-chloro-n-hexane, chloroform, carbon tetrachloride, n-pentane, n-hexane, n-heptane, n-octane, cyclohexane, cyclopentane, cyclooctane, and methylcyclohexane.

The amount (weight) of the second organic solvent introduced may be 1 to 5 times the weight of the diamine hydrochloride composition. If the introduced amount is within the above range, it is possible to prevent the use of excessive organic solvents while the yield of the final diisocyanate is high. Specifically, the second organic solvent may be introduced to the reaction in an amount of 2 to 5 times or 3 to 5 times the weight of the diamine hydrochloride composition.

The reaction temperature of the diamine hydrochloride composition and triphosgene is adjusted within a range of 115° C. to 160° C.

The reaction temperature of the diamine hydrochloride composition and triphosgene is 115° C. or higher, so that the reaction between the diamine hydrochloride and triphosgene is carried out more smoothly, which may be advantageous for increasing the yield and shortening the reaction time. In addition, if the reaction temperature of the diamine hydrochloride composition and triphosgene is 160° C. or less, it is possible to suppress the generation of impurities such as tar when the final diisocyanate is produced. For example, the reaction temperature of the diamine hydrochloride composition and triphosgene may be 115° C. to 160° C., 115° C. to 130° C., or 130° C. to 160° C.

In addition, if the reaction temperature of the diamine hydrochloride composition and triphosgene is 130° C. or lower, it may be more advantageous for suppressing impurities containing chlorine (e.g., chloromethylbenzyl isocyanate, 1,3-bis(chloromethyl)benzene, and the like). Specifically, the reaction temperature of the diamine hydrochloride composition and triphosgene may be 115° C. to 130° C. More specifically, the reaction temperature of the diamine hydrochloride composition and triphosgene may be 115° C. to 120° C.

The reaction of the diamine hydrochloride composition with triphosgene may be carried out for 5 hours to 100 hours. When the reaction time is within the above range, the reaction time is not excessive, and the production of unreacted materials due to the generation of phosgene can be minimized. Specifically, the reaction of the diamine hydrochloride composition with triphosgene may be carried out for 15 hours to 40 hours, 20 hours to 35 hours, or 24 hours to 30 hours.

As a specific example, the reaction of the diamine hydrochloride composition with triphosgene may be carried out at a temperature of 115° C. to 160° C. or 115° C. to 130° C. for 5 hours to 100 hours.

The diamine hydrochloride composition and triphosgene may be introduced to the reaction at an equivalent ratio of 1:1 to 5. When the equivalent ratio is within the above range, the reaction efficiency is high, and it is possible to prevent an increase in reaction time due to an excessive introduction. Specifically, the diamine hydrochloride composition and triphosgene may be introduced to the reaction at an equivalent ratio of 1.1.5 to 4 or 1:2 to 2.5.

Alternatively, the diamine hydrochloride composition and triphosgene may be introduced to the reaction at a molar ratio of greater than 1:0.70 to less than 0.95 or 1:0.73 to 0.90. When the molar ratio is within the above range, the reaction efficiency is high, and it is possible to prevent an increase in reaction time due to an excessive introduction. Specifically, if the molar ratio of the diamine hydrochloride composition and triphosgene is 1:0.70 or less, the reaction is not sufficiently carried out, so that the remaining amine reacts with the diisocyanate thus prepared to form urea, thereby lowering the yield and purity. In addition, if the molar ratio of the diamine hydrochloride composition and triphosgene exceeds 1:0.95, the remaining triphosgene may cause cloudiness, and the content of hydrolyzable chlorine may increase, thereby lowering the yield and purity of the diisocyanate prepared.

The hydrolyzable chlorine is a material produced as a byproduct in the reaction of the diamine hydrochloride composition and triphosgene. It may promote a deterioration in the quality such as haze and yellowing of the diisocyanate prepared, which causes cloudiness and yellowing when the final optical lens is prepared, resulting in a deterioration in the quality of the lens.

The reaction of the diamine hydrochloride composition and triphosgene may sequentially comprise (2-a) mixing the diamine hydrochloride composition with an organic solvent to obtain a first solution; (2-b) mixing triphosgene with an organic solvent to obtain a second solution; and (2-c) introducing the second solution to the first solution and stirring them.

The organic solvent in steps (2-a) and (2-b) may be the second organic solvent.

The step of obtaining the first solution may be carried out at a temperature of 115° C. to 160° C., and the step of obtaining the second solution may be carried out at a temperature of 50° C. to 70° C. For example, the step of obtaining the first solution may be carried out at 115° C. to 160° C. or 115° C. to 130° C., and the step of obtaining the second solution may be carried out at a temperature of 50° C. to 70° C. or 55° C. to 65° C.

The amount of the second organic solvent introduced in step (2-a) may be 4.2 to 4.8 times the weight of the diamine hydrochloride composition, and the amount of the second organic solvent introduced in step (2-b) may be 0.6 to 0.9 times the weight of the triphosgene. If the amount of introduction is within the above range, it is possible to prevent the use of excessive organic solvents while the yield of the final diisocyanate is high.

In such event, the introduction of the second solution and stirring may be carried out at a temperature of 115° C. to 160° C. or 115° C. to 130° C. In addition, the introduction of the second solution may be divided into two or more times for a total of 25 hours to 40 hours. In addition, here, the time for each introduction may be 5 hours to 25 hours or 10 hours to 14 hours. In addition, the time for further reaction by stirring after the introduction may be 2 hours to 5 hours, 3 hours to 4.5 hours, or 3 hours to 4 hours.

Alternatively, the reaction of the diamine hydrochloride composition and triphosgene may sequentially comprise (2a) introducing the second organic solvent to a second reactor; (2b) introducing the diamine hydrochloride composition to the second reactor and stirring them; and (2c) introducing triphosgene to the second reactor and stirring them.

In such event, the introduction of triphosgene in step (2c) may be carried out by introducing a solution in which triphosgene is dissolved in the same solvent as the second organic solvent to the reactor as divided into two or more times at a temperature of 115° C. to 160° C. or 115° C. to 130° C. for a total of 25 hours to 40 hours. In addition, here, the time for each introduction may be 5 hours to 25 hours or 10 hours to 14 hours. In addition, the time for further reaction by stirring after the introduction may be 2 hours to 5 hours or 3 hours to 4 hours.

Upon the reaction, the reaction resultant may be cooled at 90° C. to 110° C.

The resultant obtained through the reaction may be further subjected to separation, degassing, cooling, filtration, distillation, and the like.

For example, after the reaction, the reaction resultant may be subjected to degassing at 80° C. to 150° C. with the bubbling of nitrogen gas. In addition, after the degassing, it may be cooled to 10° C. to 30° C., and solids may be filtered off.

The diisocyanate composition may be obtained by distillation after the reaction of the diamine hydrochloride composition and triphosgene.

The distillation may comprise distillation to remove the second organic solvent. For example, after the reaction, the reaction resultant may be distilled at 40° C. to 60° C. for 2 hours to 8 hours to remove the second organic solvent. The pressure during the distillation may be 2.0 torr or less, 1.0 torr or less, 0.5 torr or less, or 0.1 torr or less. In addition, the second organic solvent may be recovered and recycled through the distillation.

In addition, the distillation may comprise distilling the diisocyanate. The diisocyanate composition may be obtained by distillation of the crude diisocyanate composition at a temperature of 100° C. to 130° C. If the distillation temperature is within the above range, it is more advantageous for preventing a deterioration in the physical properties of the final optical lens such as stria, cloudiness, and yellowing by effectively removing hydrolyzable chlorine compounds generated at high temperatures such as chloromethylbenzyl isocyanate (CBI) and 1,3-bis(chloromethyl)benzene. Specifically, the distillation may be carried out by setting the bottom temperature of the distiller to 100° C. to 130° C. For example, the distillation may be carried out by setting the reboiler temperature to 100° C. to 130° C.

In addition, the pressure during the distillation may be 2.0 torr or less, 1.0 torr or less, 0.5 torr or less, or 0.1 torr or less. Specifically, the distillation may comprise distillation of a diisocyanate at a temperature of 100° C. to 130° C. and a pressure of 2 torr or less.

In addition, the time for the distillation of a diisocyanate may be 1 hour or longer, 2 hours or longer, or 3 hours or longer, and may be 10 hours or shorter or 5 hours or shorter. Specifically, the distillation of a diisocyanate may be carried out for 2 hours to 10 hours.

According to the process of the above embodiment, the distillation temperature range is controlled, whereby the distillation yield may be high and the impurities in the diisocyanate composition may be very low.

The yield of the distillation of a diisocyanate may be 80% or more, specifically 85% or more, or 90% or more. In such event, the distillation yield may be calculated by measuring the amount of the diisocyanate composition upon the distillation relative to the theoretical amount of the diisocyanate composition produced from the amounts of the diamine hydrochloride composition introduced to the reaction with triphosgene.

According to the process of the above embodiment, the reaction temperature range of the diamine hydrochloride composition and triphosgene is controlled, whereby the crude diisocyanate composition before purification may contain very little impurities. Specifically, the diisocyanate composition may contain 99.0% by weight or more of the diisocyanate before the distillation of a diisocyanate. In addition, the diisocyanate composition may contain 99.9% by weight or more of the diisocyanate after the distillation of a diisocyanate.

In addition, the content of aromatic compounds having a halogen group in the diisocyanate composition may be 1,000 ppm or less.

In addition, the yield of the diisocyanate finally obtained may be 80% or more, 85% or more, or 90% or more.

Diisocyanate Composition

The diisocyanate composition prepared using a diamine hydrochloride composition and triphosgene as described above may be improved in terms of the color and haze.

The diisocyanate composition may have an APHA (American Public Health Association) color value of 20 or less or 10 or less. Specifically, the diisocyanate composition may have an APHA color value of 1 to 20 or 1 to 10.

In addition, the diisocyanate composition may have a haze of 10% or less, 5% or less, or 3% or less.

In addition, according to the above embodiment, the molar ratio of a diamine hydrochloride composition and triphosgene is controlled in the preparation of the diisocyanate composition, whereby the side reactions that may take place in the preparation of a diisocyanate composition may be suppressed, resulting in enhancements in the yield and purity of the diisocyanate.

The content of hydrolyzable chlorine that may be produced from the side reactions may be 150 ppm or less or 130 ppm or less. For example, the content of hydrolyzable chlorine may be 55 ppm to 150 ppm or 55 ppm to 130 ppm. The hydrolyzable chlorine may cause a deterioration in the physical properties such as cloudiness in the final optical lens.

In addition, the content of diisocyanate in the diisocyanate composition may be 90% by weight or more, 95% by weight or more, or 99.5% by weight or more, specifically 90% to 99.9% by weight.

In addition, the diisocyanate composition may further comprise benzyl isocyanate, methylbenzyl isocyanate, cyanobenzyl isocyanate, and the like. The total content of these components may be about 1% by weight or less.

The diisocyanate composition may comprise xylylene diisocyanate or other diisocyanates used in the preparation of optical lenses. Specifically, it may comprise at least one selected from the group consisting of orthoxylylene diisocyanate (o-XDI), metaxylylene diisocyanate (m-XDI), paraxylylene diisocyanate (p-XDI), norbornene diisocyanate (NBDI), hydrogenated xylylene diisocyanate (H6XDI), isophorone diisocyanate (IPDI), and hexamethylene diisocyanate (HDI).

According to the process of the above embodiment, the yield of diisocyanate is high, the recycling rate of organic solvents is excellent, it is environmentally friendly since highly toxic phosgene gas is not used, it is possible to react at atmospheric pressure, and a separate apparatus for pressurization or rapid cooling is not required.

Measurement of the Color and Transparency of a Reaction Solution

The step of obtaining a diisocyanate composition from the diamine hydrochloride composition and triphosgene may comprise (aa) reacting the diamine hydrochloride composition with triphosgene in a reactor to obtain a reaction solution; (ab) measuring the color and transparency of the reaction solution; and (ac) obtaining a diisocyanate composition from the reaction solution.

In the reaction of the diamine hydrochloride composition and triphosgene, the color and transparency of the reaction solution may be measured to adjust the reaction conditions.

For example, in the reaction of metaxylylenediamine hydrochloride and triphosgene to obtain metaxylylene diisocyanate, the reaction solution at the beginning of the reaction may be opaque colorless or white, and the reaction solution at the time when the reaction is ordinarily completed may be transparent or close to transparent in a light brown color.

For example, in the step of measuring the color and transparency of the reaction solution, the reaction solution may have a transparent light brown color.

Specifically, the reaction solution may have an L* value of 45 to 60, an a* value of 3 to 15, and a b* value of 15 to 30 in the CIE-LAB color coordinate. More specifically, the reaction solution may have an L* value of 50 to 55, an a* value of 5 to 10, and a b* value of 20 to 25 in the CIE-LAB color coordinate.

In addition, the reaction solution may have a transmittance of 60% or more, 70% or more, 80/or more, or 90% or more, for light having a wavelength of 550 nm. In addition, the reaction solution may have a haze of 20% or less, 10%0 or less, 5% or less, or 3% or less. Specifically, the reaction solution may have a transmittance of 70% or more for light having a wavelength of 550 nm and a haze of 10% or less. More specifically, the reaction solution may have a transmittance of 80% or more for light having a wavelength of 550 nm and a haze of 5% or less.

On the other hand, if the reaction of the metaxylylenediamine hydrochloride and triphosgene is not completed, the reaction solution may be opaque or have a precipitate, and the color may be pale, white, or colorless. In addition, if side reactions take place to a significant extent, the reaction solution may be opaque or may have a color other than light brown, for example, a dark brown or dark color.

The reaction of the diamine hydrochloride composition and triphosgene may be carried out simultaneously with the step of measuring the color and transparency of the reaction solution.

That is, while the reaction of the diamine hydrochloride composition and triphosgene is being carried out, the color and transparency of the reaction solution may be measured in real time.

In addition, for more accurate measurement, a part of the reaction solution may be collected to precisely measure the color and transparency thereof. For example, the measurement of the color and transparency of the reaction solution may be carried out by collecting a part of the reaction solution and measuring the color and transparency of the collected reaction solution.

In such event, the reaction equivalent, reaction temperature, or reaction time may be adjusted according to the color and transparency of the reaction solution. For example, the timing for terminating the reaction may be determined according to the color and transparency of the reaction solution. Specifically, the timing for terminating the reaction may come after when the reaction solution turns a transparent light brown color.

As an example, the reactor may have a viewing window, and the measurement of the color and transparency of the reaction solution may be carried out through the viewing window.

The reactor is connected to one or more stages of condensers. Once the gas generated in the reactor has been transferred to the one or more stages of condensers, the second organic solvent present in the gas may be condensed and recycled to the reactor.

The one or more stages of condensers are connected to a first scrubber and a second scrubber. The gas transferred from the reactor to the one or more stages of condensers contains hydrogen chloride gas and phosgene gas, the first scrubber may dissolve the hydrogen chloride gas in water to produce an aqueous solution, and the second scrubber may neutralize the phosgene gas with an aqueous NaOH solution.

In addition, the reactor is connected to one or more stages of distillers. The reaction solution is transferred to the one or more stages of distillers, and the one or more stages of distillers may separate the diisocyanate composition and the second organic solvent from the reaction solution.

The separated second organic solvent may be recycled for the reaction of the diamine hydrochloride composition and triphosgene.

FIG. 2 shows an example of the process equipment for the reaction of a diamine hydrochloride composition and triphosgene.

First, a first tank (T-1) is charged with a second organic solvent and triphosgene, and the temperature is maintained to be constant by refluxing hot water. The inside of a reactor (R-1) is purged with nitrogen, a second organic solvent is introduced thereto with stirring, a diamine hydrochloride composition is slowly introduced thereto, and they are stirred while the internal temperature of the reactor is maintained to be constant.

Thereafter, triphosgene in the second organic solvent is gradually introduced into the reactor (R-1) from the first tank (T-1). The introduction of triphosgene in the second organic solvent is carried out at a time or divided into two or more times. At that time, stirring is performed while the internal temperature of the reactor (R-1) is maintained to be constant. Upon completion of the introduction, an additional reaction is carried out while stirring is performed for a certain period of time. As an example, the color and transparency of the reaction solution are monitored with the naked eyes through a viewing window (G-1) provided in the reactor (R-1). As another example, the color and transparency of the reaction solution are measured with an optical device through the viewing window (G-1) provided in the reactor (R-1). The optical device may include a digital camera, a spectrometer, and optical analysis equipment.

The gas (second organic solvent, hydrogen chloride, phosgene, and the like) present inside the reactor (R-1) is transferred to a first condenser (C-1). In the first condenser (C-1), the second organic solvent is firstly condensed by cooling and recycled to the reactor (R-1), and the remaining gas is transferred to a second condenser (C-2). In the second condenser (C-2), the second organic solvent is secondly condensed by cooling and recycled to the reactor (R-1), and the remaining gas is transferred to a third condenser (C-3). In the third condenser (C-3), the second organic solvent is thirdly condensed by cooling and recycled to the reactor (R-1).

Once the second organic solvent is removed while it passes through the multi-stage condensers as described above, the remaining gas (hydrogen chloride, phosgene, and the like) is transferred to a first scrubber (S-1). In the first scrubber (S-1), hydrogen chloride gas is dissolved in water to obtain an aqueous hydrochloric acid solution and stored in a second tank (T-2), and the remaining gas is transferred to a second scrubber (S-2). In the second scrubber (S-1), phosgene (COCl$_2$) gas may be neutralized with an aqueous sodium hydroxide solution stored in a third tank (T-3) and removed.

The reaction solution obtained from the reactor (R-1) is sequentially transferred to a first distiller (D-1) and a second distiller (D-2). While it undergoes first and second distillation, the diisocyanate composition and the second organic solvent are separated from the reaction solution.

The second organic solvent separated from the reaction solution may be transferred to, and stored in, a solvent recovery apparatus (V-1). Thereafter, it may be recycled for the reaction of the diamine hydrochloride composition and triphosgene.

In addition, the diisocyanate composition separated from the reaction solution may be further subjected to filtration and drying to provide a final product.

[Process for the Preparation of an Optical Lens]

The diisocyanate prepared in the above embodiment may be combined with other components to prepare a composition for an optical material.

That is, the composition for an optical material comprises a diisocyanate prepared according to the above embodiment and a thiol or an episulfide.

The composition for an optical material may be used to prepare an optical material, specifically an optical lens. For example, the composition for an optical material is mixed and heated and cured in a mold to produce an optical lens.

The process for preparing an optical lens according to still another embodiment comprises obtaining a diisocyanate composition from the above preparation process; and mixing the diisocyanate composition with a thiol or an episulfide and polymerizing and curing the resultant in a mold.

Specifically, the process for preparing an optical lens comprises reacting a diamine with an aqueous hydrochloric acid solution to obtain a diamine hydrochloride composition; reacting the diamine hydrochloride composition with triphosgene at a temperature of 115° C. to 160° C. to obtain a diisocyanate composition; and mixing the diisocyanate composition with a thiol or an episulfide and polymerizing and curing the resultant in a mold.

Alternatively, the process for preparing an optical lens comprises reacting a diamine with an aqueous hydrochloric acid solution to obtain a diamine hydrochloride composition; reacting the diamine hydrochloride composition with triphosgene to obtain a diisocyanate composition, and mixing the diisocyanate composition with a thiol or an episulfide and polymerizing and curing the resultant in a mold, wherein the molar ratio of the diamine hydrochloride composition and triphosgene introduced to the reaction is greater than 1:0.70 to less than 0.95.

The process for preparing an optical lens comprises reacting a diamine with an aqueous hydrochloric acid solution to obtain a diamine hydrochloride composition; reacting the diamine hydrochloride composition with triphosgene to obtain a crude diisocyanate composition; distilling the crude diisocyanate composition at a temperature of 100° C. to 130° C. to obtain a diisocyanate composition, and mixing the diisocyanate composition with a thiol or an episulfide and polymerizing and curing the resultant in a mold.

The thiol may be a polythiol containing two or more SH groups. It may have an aliphatic, alicyclic, or aromatic skeleton. The episulfide may have two or more thioepoxy groups. It may have an aliphatic, alicyclic, or aromatic skeleton.

Specific examples of the thiol include bis(2-mercaptoethyl) sulfide, 4-mercaptomethyl-1,8-dimercapto-3,6-dithiaoctane, 2,3-bis(2-mercaptoethylthio)propane-1-thiol, 2,2-bis(mercaptomethyl)-1,3-propanedithiol, tetrakis(mercaptomethyl)methane, 2-(2-mercaptoethylthio)propane-1,3-dithiol, 2-(2,3-bis(2-mercaptoethylthio)propylthio)ethanethiol, bis(2,3-dimercaptopropanyl) sulfide, bis(2,3-dimercaptopropanyl) disulfide, 1,2-bis(2-mercaptoethylthio)-3-mercaptopropane, 1,2-bis(2-(2-mercaptoethylthio)-3-mercaptopropylthio)ethane, bis(2-(2-mercaptoethylthio)-3-mercaptopropyl) sulfide, bis(2-(2-mercaptoethylthio)-3-mercaptopropyl) disulfide, 2-(2-mercaptoethylthio)-3-2-mercapto-3-[3-mercapto-2-(2-mercaptoethylthio)-propylthio]propylthio-propane-1-thiol, 2,2-bis-(3-mercapto-propionyloxymethyl)-butyl ester, 2-(2-mercaptoethylthio)-3-(2-(2-[3-mercapto-2-(2-mercaptoethylthio)-propylthio]ethylthio)ethylthio)propane-1-thiol, (4R,11S)-4,11-bis(mercaptomethyl)-3,6,9,12-tetrathiatetradecane-1,14-dithiol, (S)-3-((R-2,3-dimercaptopropyl)thio)propane-1,2-dithiol, (4R,14R)-4,14-bis(mercaptomethyl)-3,6,9,12,15-pentathiaheptane-1,17-dithiol, (S)-3-((R-3-mercapto-2-((2-mercaptoethyl)thio)propyl)thio)-2-((2-mercaptoethyl)thio)propane-1-thiol, 3,3'-dithiobis(propane-1,2-dithiol), (7R,11S)-7,11-bis(mercaptomethyl)-3,6,9,12,15-pentathiaheptadecane-1,17-dithiol, (7R,12S)-7,12-bis(mercaptomethyl)-3,6,9,10,13,16-hexathiaoctadecane-1,18-dithiol, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, pentaerythritol tetrakis(3-mercaptopropionate), trimethylolpropane tris(3-mercaptopropionate), pentaethritol tetrakis(2-mercaptoacetate), bispentaerythritol-ether-hexakis(3-mercaptopropionate), 1,1,3,3-tetrakis(mercaptomethylthio)propane, 1,1,2,2-tetrakis(mercaptomethylthio)ethane, 4,6-bis(mercaptomethylthio)-1,3-dithiane, 2-(2,2-bis(mercaptodimethylthio)ethyl)-1,3-dithiane, 2,5-bismercaptomethyl-1,4-dithiane, bis(mercaptomethyl)-3,6,9-trithiaundecan-1,11-dithiol.

Preferably, the thiol may be 2-(2-mercaptoethylthio)propane-1,3-dithiol, 2,3-bis(2-mercaptoethylthio)propane-1-thiol, 2-(2,3-bis(2-mercaptoethylthio)propylthio)ethanethiol, 1,2-bis(2-mercaptoethylthio)-3-mercaptopropane, 1,2-bis(2-(2-mercaptoethylthio)-3-mercaptopropylthio)-ethane, bis(2-(2-mercaptoethylthio)-3-mercaptopropyl) sulfide, 2-(2-mercaptoethylthio)-3-2-mercapto-3-[3-mercapto-2-(2-mercaptoethylthio)-propylthio]propylthio-propane-1-thiol, 2,2'-thiodiethanethiol, 4,14-bis(mercaptomethyl)-3,6,9,12,15-pentathiahectadecane-1,17-dithiol, 2-(2-mercaptoethylthio)-3-[4-(1-{4-[3-mercapto-2-(2-mercaptoethylthio)-propoxy]-phenyl}-1-methylethyl)-phenoxy]-propane-1-thiol, pentaerythritol tetrakis(3-mercaptopropionate), pentaerythritol mercaptoacetate, trimethanolpropanetrismercaptopropionate, glycerol trimercaptopropionate, dipentaerythritol hexamercaptopropionate, or 2,5-bismercaptomethyl-1,4-dithiane. The thiol may be any one or two or more of the exemplary compounds, but it is not limited thereto.

In addition, specific examples of the episulfide include bis(β-epithiopropylthio)methane, 1,2-bis(β-epithiopropylthio)ethane, 1,3-bis(β-epithiopropylthio)propane, 1,2-bis(β-epithiopropylthio)propane, 1-(β-epithiopropylthio)-2-(β-epithiopropylthiomethyl)propane, 1,4-bis(β-epithiopropylthio)butane, 1,3-bis(β-epithiopropylthio)butane, 1-(β-epithiopropylthio)-3-(β-epithiopropylthiomethyl)butane, 1,5-bis(β-epithiopropylthio)pentane, 1-(β-epithiopropylthio)-4-(β-epithiopropylthiomethyl)pentane, 1,6-bis(β-epithiopropylthio)hexane, 1-(β-epithiopropylthio)-5-(β-epithiopropylthiomethyl)hexane, 1-(β-epithiopropylthio)-2-[(2-β-epithiopropylthioethyl)thio]ethane, 1-(β-epithiopropylthio)-2-[[2-(2-f-epithiopropylthioethyl)thioethyl]thio]ethane, tetrakis(β-epithiopropylthiomethyl)methane, 1,1,1-tris(β-epithiopropylthiomethyl)propane, 1,5-bis(β-epithiopropylthio)-2-(β-epithiopropylthiomethyl)-3-thiapentane, 1,5-bis(β-epithiopropylthio)-2,4-bis(β-epithiopropylthiomethyl)-3-thiapentane, 1-(β-epithiopropylthio)-2,2-bis(β-epithiopropylthiomethyl)-4-thiahexane, 1,5,6-tris(β-epithiopropylthio)-4-(β-epithiopropylthiomethyl)-3-thiahexane, 1,8-bis(β-epithiopropylthio)-4-(β-epithiopropylthiomethyl)-3,6-dithiaoctane, 1,8-bis(β-epithiopropylthio)-4,5-bis(β-epithiopropylthiomethyl)-3,6-dithiaoctane, 1,8-bis(β-epithiopropylthio)-4,4-bis(β-epithiopropylthiomethyl)-3,6-dithiaoctane, 1,8-bis(β-epithiopropylthio)-2,4,5-tris(β-epithiopropylthiomethyl)-3,6-dithiaoctane, 1,8-bis(β-epithiopropylthio)-2,5-bis(β-epithiopropylthiomethyl)-3,6- dithiaoctane, 1,9-bis(β-epithiopropylthio)-5-(β-epithiopropylthiomethyl)-5-[(2-β-epithiopropylthioethyl)thiomethyl]-3,7-ditianonane, 1,10-bis(β-epithiopropylthio)-5,6-bis[(2-β-epithiopropylthioethyl)thio]-3,6,9-trithiadecane, 1,11-bis(β-epithiopropylthio)-4,8-bis(β-epithiopropylthiomethyl)-3,6,9-trithiaundecane, 1,11-bis(β-epithiopropylthio)-5,7-bis(β-epithiopropylthiomethyl)-3,6,9-trithiaundecane, 1,11-bis(β-epithiopropylthio)-5,7-[(2-β-epithiopropylthioethyl)thiomethyl]-3,6,9-trithiaundecane, 1,11-bis(β-epithiopropylthio)-4,7-bis(β-epithiopropylthiomethyl)-3,6,9-trithiaundecane, 1,3-bis(β-epithiopropylthio)cyclohexane, 1,4-bis(β-epithiopropylthio)cyclohexane, 1,3-bis(β-epithiopropylthiomethyl)cyclohexane, 1,4-bis(β-epithiopropylthiomethyl)cyclohexane, bis[4-(β-epithiopropylthio)cyclohexyl]methane, 2,2-bis[4-(β-epithiopropylthio)cyclohexyl]propane, bis[4-(β-epithiopropylthio)cyclohexyl] sulfide, 2,5-bis(β-epithiopropylthiomethyl)-1,4-dithiane, 2,5-bis(β-epithiopropylthioethylthiomethyl)-1,4-dithiane, 1,3-bis(β-epithiopropylthio)benzene, 1,4-bis(β-epithiopropylthio)benzene, 1,3-bis(β-epithiopropylthiomethyl)benzene, 1,4-bis(β-epithiopropylthiomethyl)benzene, bis[4-(β-epithiopropylthio)phenyl]methane, 2,2-bis[4-(β-epithiopropylthio)phenyl]propane, bis[4-(β-epithiopropylthio)phenyl]sulfide, bis[4-(β-epithiopropylthio)phenyl] sulfone, and 4,4'-bis(β-epithiopropylthio)biphenyl.

The episulfide may be any one or two or more of the exemplary compounds, but it is not limited thereto. In addition, the episulfide may be a compound in which at least one of the hydrogens of its thioepoxy group is substituted with a methyl group.

The composition for an optical material may comprise the diisocyanate composition and the thiol or episulfide in a mixed state or in a separated state. That is, in the composition, they may be in a state of being compounded in contact with each other or separated from each other so as not to contact each other.

The composition for an optical material may comprise the thiol or episulfide and the diisocyanate composition at a weight ratio of 2:8 to 8:2, 3:7 to 7:3, or 4:6 to 6:4.

A catalyst, a chain extender, a crosslinking agent, an ultraviolet stabilizer, an antioxidant, an anti-coloring agent, a dye, a filler, a release agent, and the like may be further added depending on the purpose when the composition for an optical material and an optical lens are prepared.

The thiol or episulfide is mixed with a diisocyanate composition and other additives, which is defoamed, injected into a mold, and gradually polymerized while the temperature is gradually elevated from low to high temperatures. The resin is cured by heating to prepare an optical lens.

The polymerization temperature may be, for example, 20° C. to 150° C., particularly 25° C. to 120° C. In addition, a reaction catalyst, which is conventionally used in the production of polythiourethane, may be employed in order to control the reaction rate. Specific examples of the reaction catalyst are as exemplified above.

In addition, if required, the optical lens thus prepared may be subjected to physical or chemical treatment such as anti-reflection coating, hardness, enhancements in abrasion resistance and chemical resistance, anti-fogging, surface polishing, antistatic treatment, hard coat treatment, anti-reflection treatment, and dyeing treatment.

The optical lens prepared by the above process has excellent optical properties such as transparency, refractive index, and yellow index. For example, the optical lens may have a refractive index of 1.55 or more, specifically a refractive index of 1.55 to 1.77. Alternatively, the optical lens may have a refractive index of 1.6 or more, specifically a refractive index of 1.6 to 1.7.

In addition, the optical lens may have an Abbe number of 30 to 50, specifically 30 to 45 or 31 to 40. In addition, the optical lens may have a light transmittance of 80% or more, 85% or more, 87% or more, or 90% or more, which may be a total light transmittance. In addition, the optical lens may have a yellow index (Y.I.) of 30 or less, or less, 22 or less, or 20 or less, for example, 1 to 25 or 10 to 20. Specifically, the optical lens may have a transmittance of 85% or more and a yellow index of 20 or less. Alternatively, the optical lens may have a transmittance of 90/or more and a yellow index of 22 or less.

MODE FOR CARRYING OUT THE INVENTION

Hereinafter, more specific embodiments are illustrated, but the present invention is not limited thereto.

Examples 1-1: Preparation of a Diisocyanate Composition

Step (1): Preparation of a Diamine Hydrochloride Composition

A reactor was charged with 1,009.4 g (9.46 moles) of an aqueous solution of 35% hydrochloric acid, followed by lowering the internal temperature of the reactor to 15° C. with stirring. While the temperature of the reactor was maintained at 50° C., 600.0 g (4.4 moles) of m-XDA was introduced for 1 hour. Upon completion of the introduction, the internal temperature of the reactor was lowered to 10° C., and it was stirred for 1 hour. Thereafter, 1,320.0 g of tetrahydrofuran (THF) was introduced, and the internal temperature of the reactor was lowered to −5° C., followed by stirring for 1 hour. Upon completion of the reaction, the diamine hydrochloride composition containing m-XDA.2HCl was separated by vacuum filtration using a filter, and the filtered tetrahydrofuran was recovered for reuse. In order to remove the residual solvent and water, the separated diamine hydrochloride composition was further washed and dried at 90° C. and 0.5 torr for 4 hours.

Step (2): Preparation of a Diisocyanate Composition

Reactor A was charged with 800 g of the diamine hydrochloride composition prepared above and 3,550 g of ODCB, which was heated at about 125° C. with stirring. Reactor B was charged with 950 g of triphosgene (BTMC) and 800 g of ODCB, which was stirred at about 50° C. to 60° C. for dissolution. While the temperature was maintained at 125° C. so as not to precipitate, it was added dropwise to Reactor A over 24 hours. Upon completion of the dropwise addition, it was stirred for 3 to 4 hours. Upon completion of the reaction, nitrogen gas was blown into the solvent with bubbling at 125° C. to degas. Thereafter, it was cooled to 10° C., and the remaining solids were filtered using celite. The organic solvent (ODCB) was removed to obtain a crude diisocyanate composition containing m-XDI. Here, the removal of the organic solvent was carried out for 4 hours to 8 hours at a pressure of 0.5 torr or less and a temperature of 60° C. Thereafter, the crude diisocyanate composition obtained above was distilled for 10 hours by setting the bottom temperature of the distiller at 120° C. under a pressure of 0.5 torr or less.

Examples 1-2 to 1-4 and Comparative Examples 1-1 to 1-5

A diisocyanate composition was prepared in the same manner as in Example 1-1, except that the reaction temperature of the diamine hydrochloride composition and triphosgene was changed as shown in Table 1 below.

Preparation of an Optical Lens 49.3 parts by weight of 4,8-bis(mercaptomethyl)-3,6,9-trithiaundecane-1,11-dithiol, 50.7 parts by weight of the diisocyanate composition prepared in the Examples or the Comparative Examples, 0.01 part by weight of dibutyltin dichloride, and 0.1 part by weight of a phosphate ester release agent (ZELEC™ UN Stepan) were homogeneously mixed, which was defoamed at 600 Pa for 1 hour, filtered through a Teflon filter of 3 μm, and injected into a mold made of a glass mold and a tape. Thereafter, the mold was maintained at 25° C. for 8 hours and slowly heated to 130° C. at a constant rate over 8 hours, and polymerization was carried out at 130° C. for 2 hours. The molded article was released from the mold and subjected to further curing at 120° C. for 2 hours to obtain an optical lens.

Evaluation Method

The diisocyanate compositions and optical lenses prepared in the Examples and the Comparative Examples were evaluated as follows.

(1) Content of a Diisocyanate

The content of a diisocyanate in the diisocyanate composition was determined by gas chromatography (GC) (instrument: 6890/7890 of Agilent, carrier gas: He, injection temperature 250° C., oven temperature 40° C. to 320° C., column: HP-1, Wax, 30 m, detector: FID, 300° C.)

(2) Stria

A lens having a diameter of 75 mm with −2.00 and −8.00 D was prepared. Light from a mercury lamp as a light source was transmitted through the lens. The transmitted light was projected onto a white plate, and the presence or absence of contrast was visually checked to determine the generation of striae.

(3) Yellow Index (Y.I.)

An optical lens was prepared in the form of a cylinder with a radius of 16 mm and a height of 45 mm. Light was transmitted in the height direction to measure the yellow index. The yellow index was calculated by the following equation based on the values of x and y, which are the measurement results. Y.I.=(234x+106y)/y.

(4) Cloudiness (Haze)

The optical lens was irradiated to a projector in a darkroom to observe whether the optical lens was cloudy or had any opaque material with the naked eyes.

The results are shown in Table 1 below.

TABLE 1

| | Phosgenation reaction temp. (° C.) | Distillation yield (%) | Content of a diisocyanate in the diisocyanate composition (% by weight) | | Optical lens | | |
|---|---|---|---|---|---|---|---|
| | | | Before distillation | After distillation | Stria | Cloudiness | Y.I. |
| Ex. 1-1 | 115 | 85 | 99.5 | 99.9 | Absent | Absent | 19 |
| Ex. 1-2 | 120 | 88 | 99.6 | 99.9 | Absent | Absent | 20 |
| Ex. 1-3 | 125 | 89 | 99.6 | 99.9 | Absent | Absent | 19 |
| Ex. 1-4 | 130 | 90 | 99.4 | 99.9 | Absent | Absent | 20 |
| C. Ex. 1-1 | 90 | | Reaction not carried out | | | | |
| C. Ex. 1-2 | 100 | | Reaction not carried out | | | | |
| C. Ex. 1-3 | 140 | 86 | 98.1 | 99.5 | Absent | Slight haze | 26 |
| C. Ex. 1-4 | 160 | 84 | 98.3 | 99.6 | Absent | Slight haze | 26 |
| C. Ex. 1-5 | 180 | 80 | 97.5 | 98.5 | Absent | Slight haze | 28 |

As can be seen from Table 1 above, in Examples 1-1 to 1-4 in which the reaction temperature of the diamine hydrochloride composition and triphosgene was adjusted to 100° C. to 130° C., the distillation yield and the content of a diisocyanate in the composition were excellent. The final optical lenses prepared therefrom were improved in striae, cloudiness, and yellow index.

In contrast, in Comparative Examples 1-1 and 1-2 in which the reaction temperature was less than 100° C., the reaction was not carried out. In Comparative Examples 1-3 to 1-5 in which the reaction temperature exceeded 130° C., the distillation yield and the content of a diisocyanate in the composition were poor. The final optical lenses prepared therefrom had cloudiness or yellowing.

Examples 2-1: Preparation of a Diisocyanate Composition

Step (1): Preparation of a Diamine Hydrochloride Composition

A reactor was charged with 1,009.4 g (9.46 moles) of an aqueous solution of 35% hydrochloric acid, followed by lowering the internal temperature of the reactor to 15° C. with stirring. While the temperature of the reactor was maintained at 60° C., 600.0 g (4.4 moles) of m-XDA was introduced for 1 hour. Upon completion of the introduction, the internal temperature of the reactor was lowered to 10° C., and it was stirred for 1 hour. Thereafter, 1,500.0 g of tetrahydrofuran (THF) was introduced, and the internal temperature of the reactor was lowered to −5° C., followed by stirring for 1 hour. Upon completion of the reaction, the diamine hydrochloride composition containing m-XDA.2HCl was separated by vacuum filtration using a filter, and the filtered tetrahydrofuran was recovered for reuse. In order to remove the residual solvent and water, the residual solvent and water were removed from the separated diamine hydrochloride composition at 90° C., and it was vacuum dried at 0.5 torr for 4 hours.

Step (2): Preparation of a Diisocyanate Composition

Reactor A was charged with 800 g of the diamine hydrochloride composition prepared above and 3,550 g of ODCB, which was heated at about 125° C. with stirring. Reactor B was charged with 950 g of a triphosgene (BTMC) composition and 800 g of orthodichlorobenzene (ODCB), which was stirred at about 60° C. for dissolution. While the temperature was maintained at 125° C. so as not to precipitate, it was added dropwise to Reactor A over 24 hours. Upon completion of the dropwise addition, it was stirred for 4 hours. Upon completion of the reaction, nitrogen gas was blown into the solvent with bubbling at 125° C. to degas.

Thereafter, it was cooled to 10° C., and the remaining solids were filtered using celite. The organic solvent (ODCB) was removed, and distillation was carried out to obtain a diisocyanate composition containing m-XDI. Here, the removal of the organic solvent was carried out for 8 hours at a pressure of 0.5 torr or less and a temperature of 60° C. The distillation was carried out for 10 hours at a pressure of 0.5 torr or less and a temperature of 120° C.

Examples 2-2 to 2-4 and Comparative Examples 2-1 to 2-4

A diisocyanate composition was prepared in the same manner as in Example 2-1, except that the molar ratio of the diamine hydrochloride and triphosgene was changed as shown in Table 2 below.

TABLE 2

|  | Molar ratio of diamine hydrochloride and triphosgene |
|---|---|
| Example 2-1 | 1:0.84 |
| Example 2-2 | 1:0.90 |
| Example 2-3 | 1:0.88 |
| Example 2-4 | 1:0.73 |
| Comparative Example 2-1 | 1:0.70 |
| Comparative Example 2-2 | 1:0.67 |
| Comparative Example 2-3 | 1:0.95 |
| Comparative Example 2-4 | 1:1.00 |

Preparation of an Optical Lens 49.3 parts by weight of 4,8-bis(mercaptomethyl)-3,6,9-trithiaundecane-1,11-dithiol, 50.7 parts by weight of the diisocyanate composition prepared in the Examples or the Comparative Examples, 0.01 part by weight of dibutyltin dichloride, and 0.1 part by weight of a phosphate ester release agent (ZELEC® UN Stepan) were homogeneously mixed, which was defoamed at 600 Pa for 1 hour to prepare a polymerizable composition.

The polymerizable composition was filtered through a Teflon filter of 3 µm and injected into a mold made of a glass mold and a tape. The mold was maintained at 10° C. to 25° C. for 8 hours and slowly heated to 130° C. at a constant rate over 8 hours, and polymerization was carried out at 130° C. for 2 hours. The molded article was released from the mold and subjected to further curing at 120° C. for 2 hours to obtain an optical lens.

<Evaluation Method>

The Examples and the Comparative Examples were evaluated as follows.

(1) Content of a Diisocyanate

The content of a diisocyanate in the diisocyanate composition was determined by gas chromatography (GC) (instrument: 6890/7890 of Agilent, carrier gas: He, injection temperature 250° C., oven temperature 40° C. to 320° C., column: HP-1, Wax, 30 m, detector: FID, 300° C.)

(2) Content of Hydrolyzable Chlorine

It was measured by the method for determining hydrolyzable chlorine in Part 3 of the Test Method for Aromatic Isocyanates as Plastic Polyurethane Raw Materials specified in JIS K1603-3 (2007).

(3) Stria

A lens having a diameter of 75 mm with −2.00 and −8.00 D was prepared. Light from a mercury lamp as a light source was transmitted through the lens. The transmitted light was projected onto a white plate, and the presence or absence of contrast was visually checked to determine the generation of striae.

(4) Cloudiness

The lens was irradiated to a projector in a darkroom to observe whether the lens was cloudy or had any opaque material with the naked eyes. If the lens neither was cloudy nor had any opaque material, it was evaluated as Absent (no cloudiness). If it was cloudy or had any opaque material, it was evaluated as Present (cloudiness).

(5) Yellow Index (Y.I.)

An optical lens was prepared in the form of a cylinder with a radius of 16 mm and a height of 45 mm. Light was transmitted in the height direction to measure the yellow index. The yellow index was calculated by the following equation based on the values of x and y, which are the measurement results.

$Y.I.=(234x+106y)/y$

The evaluation results of the Examples and the Comparative Examples are shown in Tables 3 and 4 below.

TABLE 3

|  | Diisocyanate composition | | |
|---|---|---|---|
|  | Distillation yield (%) | Content of a diisocyanate (% by weight) | Content of hydrolyzable chlorine (ppm) |
| Example 2-1 | 88 | 99.9 | 68 |
| Example 2-2 | 91 | 99.9 | 110 |
| Example 2-3 | 89 | 99.9 | 84 |
| Example 2-4 | 86 | 99.9 | 55 |
| Comparative Example 2-1 | 77 | 99.8 | 54 |
| Comparative Example 2-2 | 65 | 99.7 | 45 |
| Comparative Example 2-3 | 90 | 99.7 | 215 |
| Comparative Example 2-4 | 91 | 99.7 | 890 |

TABLE 4

|  | Optical lens | | |
|---|---|---|---|
|  | Stria | Cloudiness | Y.I. |
| Example 2-1 | Absent | Absent | 19 |
| Example 2-2 | Absent | Absent | 22 |
| Example 2-3 | Absent | Absent | 19 |
| Example 2-4 | Absent | Absent | 19 |
| Comparative Example 2-1 | Absent | Present | 20 |
| Comparative Example 2-2 | Absent | Present | 21 |
| Comparative Example 2-3 | Absent | Present | 25 |
| Comparative Example 2-4 | Absent | Present | 28 |

As can be seen from Tables 3 and 4 above, in Examples 241 to 2-4 in which the molar ratio of the diamine hydrochloride composition and triphosgene was adjusted to greater than 1:0.70 to less than 0.95, the content of hydrolyzable chlorine was adjusted to 150 ppm or less. The final optical lenses prepared therefrom were excellent in striae, cloudiness, and yellow index.

In contrast, in Comparative Examples 2-1 to 2-4 in which the molar ratio of the diamine hydrochloride composition and triphosgene failed to meet the range of greater than 1:0.70 to less than 0.95, cloudiness occurred although the content of hydrolyzable chlorine was 150 ppm or less in Comparative Examples 2-1 and 2-2; and the content of the hydrolyzable chlorine exceeded 150 ppm, as well as it was poor in terms of cloudiness and yellowing in Comparative Examples 2-3 and 2-4.

Examples 3-1: Preparation of a Diisocyanate Composition

Step (1): Preparation of a Diamine Hydrochloride Composition

A reactor was charged with 1,009.4 g (9.46 moles) of an aqueous solution of 35% hydrochloric acid, followed by lowering the internal temperature of the reactor to 15° C. with stirring. While the temperature of the reactor was maintained at 50° C., 600.0 g (4.4 moles) of m-XDA was introduced for 1 hour. Upon completion of the introduction, the internal temperature of the reactor was lowered to 10° C., and it was stirred for 1 hour. Thereafter, 1,320.0 g of tetrahydrofuran (THF) was introduced, and the internal temperature of the reactor was lowered to −5° C., followed by stirring for 1 hour. Upon completion of the reaction, the diamine hydrochloride composition containing m-XDA.2HCl was separated by vacuum filtration using a filter, and the filtered tetrahydrofuran was recovered for reuse. In order to remove the residual solvent and water, the separated diamine hydrochloride composition was further washed and dried at 90° C. and 0.5 torr for 4 hours.

Step (2): Preparation of a Diisocyanate Composition

Reactor A was charged with 800 g of the diamine hydrochloride composition prepared above and 3,550 g of ODCB, which was heated at about 125° C. with stirring. Reactor B was charged with 950 g of triphosgene (BTMC) and 800 g of ODCB, which was stirred at about 60° C. for dissolution. While the temperature was maintained at 125° C. so as not to precipitate, it was added dropwise to Reactor A over 24 hours. Upon completion of the dropwise addition, it was stirred for 4 hours. Upon completion of the reaction, nitrogen gas was blown into the solvent with bubbling at 125° C. to degas. Thereafter, it was cooled to 10° C., and the remaining solids were filtered using celite. The organic solvent (ODCB) was removed to obtain a crude diisocyanate composition containing m-XDI. Here, the removal of the organic solvent was carried out for 8 hours at a pressure of 0.5 torr or less and a temperature of 60° C.

Thereafter, the crude diisocyanate composition obtained above was subjected to simple distillation for 8 hours by setting the bottom temperature of the distiller at 100° C. under a pressure of 0.5 torr or less to obtain the final diisocyanate composition.

Examples 3-2 to 3-4 and Comparative Examples 3-1 to 3-5

A diisocyanate composition was prepared in the same manner as in Example 3-1, except that the bottom temperature of the distiller was changed as shown in Table 5 below.

Preparation of an Optical Lens 49.3 parts by weight of 4,8-bis(mercaptomethyl)-3,6,9-trithiaundecane-1,11-dithiol, 50.7 parts by weight of the diisocyanate composition prepared in the Examples or the Comparative Examples, 0.01 part by weight of dibutyltin dichloride, and 0.1 part by weight of a phosphate ester release agent (ZELEC™ UN Stepan) were homogeneously mixed, which was defoamed at 600 Pa for 1 hour, filtered through a Teflon filter of 3 μm, and injected into a mold made of a glass mold and a tape. Thereafter, the mold was maintained at 25° C. for 8 hours and slowly heated to 130° C. at a constant rate over 8 hours, and polymerization was carried out at 130° C. for 2 hours. The molded article was released from the mold and subjected to further curing at 120° C. for 2 hours to obtain an optical lens.

Evaluation Method

The diisocyanate compositions and optical lenses prepared in the Examples and the Comparative Examples were evaluated as follows.

(1) Content of a Diisocyanate

The content of a diisocyanate in the diisocyanate composition was determined by gas chromatography (GC) (instrument: 6890/7890 of Agilent, carrier gas: He, injection temperature 250° C., oven temperature 40° C. to 320° C., column: HP-1, Wax, 30 m, detector: FID, 300° C.)

(2) Stria

A lens having a diameter of 75 mm with −2.00 and −8.00 D was prepared. Light from a mercury lamp as a light source was transmitted through the lens. The transmitted light was projected onto a white plate, and the presence or absence of contrast was visually checked to determine the generation of striae.

(3) Yellow Index (Y.I.)

An optical lens was prepared in the form of a cylinder with a radius of 16 mm and a height of 45 mm. Light was transmitted in the height direction to measure the yellow index. The yellow index was calculated by the following equation based on the values of x and y, which are the measurement results. Y.I.=(234x+106y)/y.

(4) Cloudiness (Haze)

The optical lens was irradiated to a projector in a darkroom to observe whether the optical lens was cloudy or had any opaque material with the naked eyes.

The results are shown in Table 5 below.

TABLE 5

| | Bottom temp. of distiller (° C.) | Distillation yield (%) | Content of a diisocyanate in the diisocyanate composition | | Optical lens | | |
|---|---|---|---|---|---|---|---|
| | | | Before distillation | After distillation | Stria | Cloudiness | Y.I. |
| Ex. 3-1 | 100 | 82 | 99.3 | 99.9 | Absent | Absent | 19 |
| Ex. 3-2 | 110 | 86 | 99.3 | 99.9 | Absent | Absent | 19 |
| Ex. 3-3 | 120 | 89 | 99.3 | 99.9 | Absent | Absent | 19 |
| Ex. 3-4 | 130 | 90 | 99.3 | 99.9 | Absent | Absent | 20 |
| C. Ex. 3-1 | 80 | 52 | 99.3 | 99.9 | Absent | Absent | 19 |
| C. Ex. 3-2 | 90 | 73 | 99.3 | 99.9 | Absent | Absent | 19 |
| C. Ex. 3-3 | 140 | 91 | 99.3 | 99.6 | Absent | Slight haze | 24 |
| C. Ex. 3-4 | 160 | 92 | 99.3 | 99.2 | Absent | Slight haze | 25 |
| C. Ex. 3-5 | 180 | 95 | 99.3 | 98.9 | Absent | Haze | 26 |

As can be seen from the above Table, in Examples 3-1 to 3-4 in which the crude diisocyanate composition obtained as a result of the reaction of a diamine hydrochloride composition and triphosgene was distilled at a bottom temperature of 100° C. to 130° C., the distillation yield and the content of a diisocyanate in the composition were excellent. The final optical lenses prepared therefrom were improved in striae, cloudiness, and yellow index.

In contrast, in Comparative Examples 3-1 and 3-2 in which the bottom temperature of the distiller fell outside the range of 100° C. to 130° C., the distillation yield and the content of a diisocyanate in the composition were poor. The final optical lenses prepared therefrom had cloudiness or yellowing.

The invention claimed is:

1. A process for preparing a diisocyanate composition, which comprises:
   (1) reacting a diamine with an aqueous hydrochloric acid solution to obtain a diamine hydrochloride composition; and
   (2) reacting the diamine hydrochloride composition with triphosgene to obtain a diisocyanate composition,
   wherein the reaction of step (2) is carried out at a temperature of 115° C. to 160° C., or the molar ratio of the diamine hydrochloride composition and triphosgene introduced to the reaction of step (2) is greater than 1:0.70 and less than 1:0.95,
   wherein the reaction of the diamine hydrochloride composition and triphosgene of step (2) sequentially comprises:
   (2-a) mixing the diamine hydrochloride composition with an organic solvent to obtain a first solution;
   (2-b) mixing triphosgene with the organic solvent to obtain a second solution; and
   (2-c) introducing the second solution to the first solution and stirring them, wherein the introduction of the second solution and stirring is carried out at a temperature of 115° C. to 160° C., and
   the organic solvent is introduced to the reaction in an amount of 4.2 to 4.8 times the weight of the diamine hydrochloride composition, or
   the organic solvent is introduced to the reaction in an amount of 0.6 to 0.9 times the weight of the triphosgene.

2. The process for preparing a diisocyanate composition of claim 1, wherein the content of aromatic compounds having a halogen group in the diisocyanate composition is 1,000 ppm or less,
   the diisocyanate composition is obtained by distillation after the reaction of step (2), and
   the distillation comprises distillation of a diisocyanate at a temperature of 100° C. to 150° C. and a pressure of 2 torr or less.

3. The process for preparing a diisocyanate composition of claim 2, wherein the diisocyanate composition comprises 99.0% by weight or more of the diisocyanate before the distillation of diisocyanate,
   the diisocyanate composition comprises 99.9% by weight or more of the diisocyanate after the distillation of diisocyanate, and
   the yield of the distillation of a diisocyanate is 85% or more.

4. The process for preparing a diisocyanate composition of claim 1, wherein the diamine is xylylenediamine, and the diisocyanate composition comprises xylylene diisocyanate.

5. The process for preparing a diisocyanate composition of claim 1, wherein in step (1), after the reaction of the diamine composition and the aqueous hydrochloric acid solution, a first organic solvent is further introduced to obtain the diamine hydrochloride composition in a solid phase.

6. The process for preparing a diisocyanate composition of claim 1, wherein the aqueous hydrochloric acid solution has a concentration of 20% by weight to 45% by weight.

7. The process for preparing a diisocyanate composition of claim 2, wherein the diisocyanate composition comprises hydrolyzable chlorine in an amount of 150 ppm or less after the distillation of a diisocyanate.

8. A process for preparing a diisocyanate composition, which comprises:
   (1) reacting a diamine with an aqueous hydrochloric acid solution to obtain a diamine hydrochloride composition;
   (2-1) reacting the diamine hydrochloride composition with triphosgene to obtain a crude diisocyanate composition; and
   (2-2) distilling the crude diisocyanate composition at a temperature of 100° C. to 130° C. to obtain a diisocyanate composition,
   wherein the reaction of the diamine hydrochloride composition and triphosgene of step (2-1) sequentially comprises:
   (2-a) mixing the diamine hydrochloride composition with an organic solvent to obtain a first solution;
   (2-b) mixing triphosgene with the organic solvent to obtain a second solution; and
   (2-c) introducing the second solution to the first solution and stirring them, wherein the introduction of the second solution and stirring is carried out at a temperature of 115° C. to 160° C., and
   the organic solvent is introduced to the reaction in an amount of 4.2 to 4.8 times the weight of the diamine hydrochloride composition, or
   the organic solvent is introduced to the reaction in an amount of 0.6 to 0.9 times the weight of the triphosgene.

9. The process for preparing a diisocyanate composition of claim 8, wherein the distillation in step (2-2) is carried out by setting the bottom temperature of a distiller at 100° C. to 130° C. under a pressure of 2.0 torr or less for 2 hours to 10 hours,
   the process further comprising degassing, before step (2-2), the resultant of the reaction of step (2-1) at 80° C. to 150° C. with the bubbling of nitrogen gas, or
   distilling, before step (2-2), the resultant of the reaction of step (2-1) at 40° C. to 60° C. for 2 hours to 8 hours.

10. The process for preparing a diisocyanate composition of claim 8, wherein the yield of the distillation of a diisocyanate is 80% or more, and the diisocyanate composition, after the distillation in step (2-2), comprises the diisocyanate in an amount of 99.9% by weight or more.

* * * * *